United States Patent [19]

Antoniades

[11] Patent Number: 4,479,896
[45] Date of Patent: Oct. 30, 1984

[54] METHOD FOR EXTRACTION LOCALIZATION AND DIRECT RECOVERY OF PLATELET DERIVED GROWTH FACTOR

[76] Inventor: Harry N. Antoniades, 21 Magnolia Ave., Newton, Mass. 02158

[21] Appl. No.: 512,315

[22] Filed: Jul. 8, 1983

Related U.S. Application Data

[63] Continuation of Ser. No. 329,668, Dec. 11, 1981, abandoned.

[51] Int. Cl.³ .............................................. C07G 7/00
[52] U.S. Cl. ............................ 260/112 B; 260/112 R; 424/101
[58] Field of Search ...................... 260/112 R, 112 B; 424/101

[56] References Cited

PUBLICATIONS

Proc. Natl. Acad. Sci. USA, vol. 76, No. 8, pp. 3722–3726, 1979, Heldin et al.
Proc. Natl. Acad. Sci. USA, vol. 76, No. 4, pp. 1809–1813, 1979, Antoniades et al.
Biochimica et Biophysica Acta, 560, (1979), 217–241, Scher et al.

*Primary Examiner*—Howard E. Schain
*Attorney, Agent, or Firm*—David Prashker

[57] ABSTRACT

A process for the localization and direct recovery of active platelet derived growth factor (PDGF) from stained sodium dodecyl sulfate/polyacrylamide gels is provided. This technique allows the user to identify and obtain purified PDGF peptides without loss of active material or special instrumentation.

12 Claims, 3 Drawing Figures

METHOD FOR EXTRACTION LOCALIZATION AND DIRECT RECOVERY OF PLATELET DERIVED GROWTH FACTOR

This application is a continuation of application Ser. No. 329,668, filed Dec. 11, 1981 now abandoned.

FIELD OF THE INVENTION

The invention deals generally with protein extraction methods and is particularly concerned with a process for the localization and direct recovery of a proteinaceous growth factor found in platelets.

BACKGROUND OF THE INVENTION

Platelet Derived Growth Factor (PDGF) is a hormonal peptide normally found in human blood platelets and is indispensible for the growth of connective tissue cells, fibroblasts, in synthetic tissue culture media. Although initially isolated from blood serum, subsequent studies have shown this polypeptide is stored in the alpha-grannules of blood platelets, is transported throughout the vascular system by these cells, and is discharged into the serum during blood clotting or after traumatic vascular injury. The concentration of PDGF in normal human blood is approximately 50 nanograms of PDGF per milliliter of sera.

Two forms of PDGF have been isolated, PDGF-I which has a molecular weight of approximately 35,000 daltons and PDGF-II which has a molecular weight of about 32,000 daltons. Both forms of PDGF are biologically active cationic polypeptides, remain stable at 100° C., and have an isoelectric point (pI) of 9.8. Each PDGF form may be reduced with mercaptoethanol into two component polypeptide chains of approximately 13,000 to 14,000 daltons and 17,000 to 18,000 daltons respectively. The component polypeptide chains of each PDGF form are stable in strong acid (pH 2.0), 8N urea, and 4N guanidine-HCl. The reduction of either type of PDGF into its component chains destroys all specific biological activity. None of these reduced component polypeptide chains individually are biologically active as growth promoting factors.

The biological activity of PDGF and protein fractions containing PDGF is measured by the ability of the polypeptide fraction to specifically induce DNA synthesis in confluent Ba1B/C-3T3 (clone A 31) cells. Biologically active PDGF stimulates the synthesis of DNA and increases the rate at which fibroblasts undergo cell division. Assays measuring stimulation activity are performed in the presence of 5% platelet-poor plasma which is necessary for the expression of an optimal response. Plasma which is deficient in platelets does not stimulate the growth of fibroblasts in artificial culture media. Such platelet deficient plasma has been shown to contain little or no PDGF. The addition of PDGF or protein fractions containing some PDGF to such platelet deficient serum, however, restores the ability of such plasma to stimulate DNA replication and cell division of normal fibroblasts in culture. The increase of DNA synthesis is empirically determined either by autoradiography as described in the publications of Scher, Stathakos, Antoniades, *Nature* (London), 247:279 (1974) and Pledger, Stiles, Antoniades, and Scher, *Proc. Natl. Acad. Sci. USA*, 74:4481–4485 (1977) or by measuring the uptake of acid-insoluble $H^3$-thymidine by the cells in culture as described in the publication of Antoniades, Stathakos and Scher, *Proc. Natl. Acad. Sci. USA*, 72:2635–2639 (1975). This specific biological activity of PDGF is measured in units defined by convention as the quantity, in picograms, required to induce 50% of the cells in culture to synthesize DNA.

More detailed information regarding the properties and characteristics of PDGF may be found in these publications: Antoniades and Scher, "Growth Factors Derived from Human Serum, Platelets, and Pituitary: Properties and Immunologic Cross-Reactivity", National Cancer Monograph No. 48, Third Decennial Review Conference: Cell, Tissue and Organ Culture, Lake Placid, N.Y., Sept. 13–17, 1976; Antoniades, Stathakos, and Scher, "Isolation of a Cationic Polypeptide from Human Serum that Stimulates Proliferation of 3T3 Cells", Biochemistry, 72:2635–2639 (1975); Scher, Shepard, Antoniades and Stiles, "Platelet-Derived Growth Factor and the Regulation of the Mammalian Fibroblast Cell Cycle", Biochem. Biophys. Acta 560:217–241 (1979); and Kaplan, Chao, Stiles, Antoniades, and Scher, "Platelet Alpha Grannules Containing a Growth Factor for Fibroblasts", Blood 53:1043–1052 (1979).

Two methods for the extraction of PDGF from platelets are presently known and described in the publications of Heldin, Westermark, and Wasteson, "Platelet-Derived Growth Factor: Purification and Partial Characterization", *Proc. Natl. Acad. Sci. USA*, 76:3722–3726 (1979) and Antoniades, Scher, and Stiles, "Purification of Human Platelet-Derived Growth Factor", *Proc. Natl. Acad. Sci. USA*, Vol. 76:1809–1813 (1979). The Heldin procedure prepares a platelet lysate and utilizes charge fractionation, hydrophobic chromatography, and two different types of size separation to yield a PDGF containing protein fraction which is approximately 90% pure. This semi-pure protein fraction shows an increase in specific biologically activity of about 8,000 times the specific activity of normal plasma and represents approximately 5% of the original starting material. This method, however, does not allow for unaided visual identification of the polypeptide. The PDGF fraction is identifiable only by using a fluorescent microscope or similar instrument able to detect fluorescent labeled polypeptides. The Antoniades procedure prepares a boiled platelet lysate precipitant and utilizes two different types of charge fractionation and two different forms of size separation to yield a purified homogeneous PDGF having 20,000,000 times the specific biological activity of unfractionated human sera. This homogeneous PDGF represents a total recovery of about 1.5% of the starting quantity of platelet materials. This method, however, requires a loss of some of the PDGF to staining procedures in order to identify which polypeptides constitute the PDGF fraction. It will be appreciated that neither the Heldin nor Antoniades method provides a non-instrument method for the localization of the PDGF fraction which can then be directly recovered as a whole without loss of material for identification purposes.

SUMMARY OF THE INVENTION

The present invention provides a process for extracting, localizing, and directly recovering a platelet derived growth factor comprising the steps of precipitating the platelet derived growth factor (PDGF) fraction from the internal contents of platelets, separating this fraction from the residual precipitant, purifying this fraction to homogenity, isolating the PDGF fraction as a localized band using gel electrophoresis means, staining the localized band with dye reagent means, excising the stained band as a gel slice, and eluting the stained PDGF from the excised gel. This process permits the identification of platelet derived growth factor as a chromophoric band which is biologically active and which may be eluted from the gel without any loss of material.

DESCRIPTION OF THE DRAWING

The invention will be more fully understood from the following detailed description taken in conjunction with the accompanying drawing in which.

DETAILED DESCRIPTION OF THE PREFERRED EMBODIMENTS

Figures 1, 2, 3:
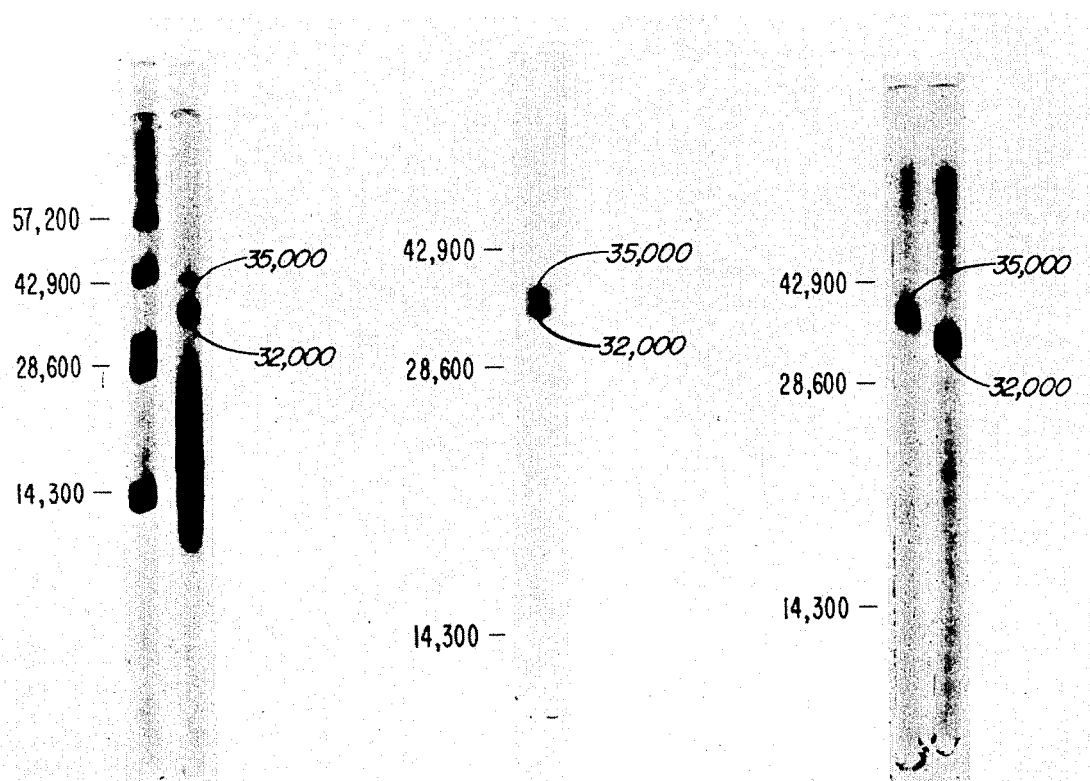
FIG. 1 is a view of unreduced platelet derived growth factor obtained after electrophoresis on 12% polyacrylamide gel followed by staining with Commassie Blue stain.
FIG. 2 is a detailed view of Type I and II PDGF on 15% polyacrylamide gel after electrophoresis and staining.
FIG. 3 is a detailed view of Type I and II PDGF isolated separately on individual 15% polyacrylamide gels after electrophoresis and staining.

The present invention is a process comprising a number of general steps, some of which require different reagents and a substantial number of individual manipulations as the preferred technique. In order to moe easily comprehend the process comprising the invention, each step has been individually entitled.

The protocol for the localization and direct recovery of purified platelet derived growth factor (hereinafter DPGF) utilizes an aqueous suspension of platelets as the raw material. Clinically outdated human platelets obtained from hospital blood banks or other similar blood donation centers are the preferred source of platelets because these centers consistently have large stocks of platelets on hand which are no longer fit for human use. These platelet stocks would otherwise be thrown away and in comparison, other sources of platelets would be prohibitively expensive.

To prepare an aqueous suspension of platelets, several units of clinically outdated platelets are pooled together as one volume and concentrated by centrifugation at 3,200 times gravity for 30 minutes. A unit of platelets is defined by convention as that quantity of platelets present in 500 milliliters (1 unit) of whole blood. The platelets are first washed with 9 times their volume of a solution comprising 17 mM Tris.HCl adjusted to pH 7.5, 0.15M NaCl and 0.1% (w/v) glucose. This first wash is followed by a wash with an equal volume of buffer solution comprising a mixture of 8 grams citric acid monohydrate, 22 grams of dextrose, and 26 grams of sodium citrate made up to a 1 liter volume with distilled water. This first and second wash is then repeated in sequence. The platelets, now thoroughly washed, are again concentrated by centrifugation at 3,200 times gravity for 30 minutes and transferred into plastic receptacles containing a minimum volume of a reagent fluid comprising 0.01M sodium phosphate and 0.08M NaCl previously adjusted to pH 7.4. This washed aqueous platelet suspension may be stored at $-15°$ C. indefinitely and later thawed for use as the source of PDGF. All further manipulations employing these washed platelet suspensions are to be conducted at 4° C. using plastic containers unless otherwise stated.

A. Precipitation of Platelet Proteins

The specific conditions and volumes described below apply for a specific initial amount of platelets, 500 units. For larger quantities, the conditions must be adjusted to handle the increased amounts of proteins during fractionation.

In order to extract PDGF polypeptides from the platelets, the washed platelet suspensions are lysed and their internal contents fractionally precipitated by the sequential addition of aqueous and organic reagents. The washed platelet suspensions are combined with from 2 to 5 milliliters per original platelet unit of a primary fractionating reagent comprising a mixture of 1M NaCl and 1M acetic acid. The mixture of platelets and primary fractionating reagent is stirred and held at 2°–5° C. overnight to form a primary supernatant fluid and a primary percipitant. The mixture is then centrifuged at 3,200 times gravity and the primary supernatant fluid decanted and stored. In the preferred method, this sequence is repeated twice more. Another 2–5 milliliters of primary fractionating reagent per platelet unit is therefore added to the primary precipitant. The reaction mixture is stirred for several hours at 2°–5° C. and again centrifuged at 3,200 times gravity. As before, the primary supernatant fluid is decanted and stored. The third extraction of the primary precipitant may be performed as herein described and a third primary supernatant fluid obtained. The primary precipitant may then be discarded.

The three primary supernatant fluids are intermixed as one volume and brought to a volumetric concentration of 75% alcohol with an alcoholic reagent, preferably ethanol. This mixture is allowed to rest undisturbed at 2°–5° C. overnight so that a secondary precipitant and a secondary supernatant fluid may be formed. The secondary supernatant is collected gently and the secondary precipitant centrifuged to release any retained fluid which is added to the previously collected secondary supernatant. The secondary precipitant may be discarded thereafter.

The total volume of secondary supernatant fluid is then slowly combined with two equal volumes of an organic precipitating reagent preferably acetone, under continuous stirring conditions. This mixture is allowed to stand undisturbed for approximately 24 hours during which a large quantity of a tertiary precipitant is formed. The tertiary supernatant fluid is decanted and discarded. The tertiary precipitant, however, is subsequently transferred to a glass container, centrifuged to release any retained fluid, and placed under gentle vacuum to remove the excess liquid. Thereafter, the tertiary precipitant is dissolved in a minimum volume of water and dialyzed against several changes of 1M acetic acid. Following dialysis, any remaining precipitant is removed by centrifugation and discarded. The dialyzed supernatant fluid containing the PDGF is then lyophilized.

Although the preferred composition and concentration of the primary fractionating reagent, the alcoholic reagent, and the organic precipitating reagent are identified herein, it is understood that substitute reagent compositions and variances in reagent concentrations may be employed when practicing the invention. Inorganic salts other than sodium chloride and weak organic acids other than acetic acid may be combined and used as the primary fractionating reagent. A broad range of alcohols other than ethanol may also be used as the alcoholic reagent. Furthermore, organic precipitating reagents other than acetone which precipitate a polypepttide fraction having DNA stimulating ability are equivalent substitutes. Similarly, the concentrations of the preferred or substituted precipitating reagents may be varied as desired so long as a biologically active PDGF containing precipitant is obtained.

B. Separation of the Polypeptide Fraction Comprising PDGF

The PDGF in the lyophilized protein must be first separated from the other constituents before purification can be achieved. For this purpose, the lyophilized protein preparation is first dissolved in a minimal volume of chromatographic fluid comprising 0.08M NaCl and 0.01M sodium phosphate. The pH of this chromatographic fluid has been adjusted to pH 7.4 by the slow addition of 1M NaOH under continuous stirring conditions. A protein containing PDGF solution is then passed through a prepared 2 liter glass column containing a bed volume of CM-Sephadex C-50 which was previously equilibrated with chromatography fluid. The dimension of the column depends on the amount of original platelet material. The 2 liter column used herein applies to a preparation of 500 platelet units. For larger pools of platelets larger columns are used.

After allowing sufficient time for the protein solution to become adsorbed to the Sephadex bed, the column is washed with 6 bed volumes of chromatographic fluid. The PDGF containing fraction is then eluted from the column by repeated washing with NaCl solution having an increasing gradient ranging from 0.0 to 1.0M. The biologically active fractions eluted from the column are pooled together as separated, but impure, PDGF polypeptide fractions, dialyzed against several changes of 1.0M acetic acid and then lyophilized in plastic tubes.

It is understood that ion exchange chromatography permits the use of alternative chromatographic fluids differing in composition and concentration from that described herein. Similarly, the chromatographic column may be packed with a broad variety of gels, particulate matter, and ion charged modulating fluids varying from the preferred Sephadex gel bed. All of these alternatives and substitutions are understood to be within the scope of the present invention.

C. Purification of PDGF

A two part technique is the preferred method for purifying the separated PDGF fraction. Initially, the lyophilized PDGF protein fraction is dissolved in a minimum volume of 1M acetic acid. 0.5-0.8 milliliter aliquots of this protein solution are applied to a 100 milliliter glass column containing a bed volume of Bio-Gel P-150 (mesh 100-200) which has been equilibrated previously with 1M acetic acid. After allowing sufficient time for the solution to filter through the Bio-Gel bed, the PDGF fraction is eluted with 1M acetic acid. If 500 platelet units are used as the starting material, about 50 milliliters of 1M acetic acid are needed to work the column. The biologically active protein fractions are then pooled together as one volume. Again, based on 500 platelet units, about 10 milligrams of protein are recovered in 40 milliliters of acetic acid eluant.

Subsequently, the partially purified PDGF concentrate obtained from the Bio-Gel P-150 filtration is dialyzed against a reagent fluid comprising 1M NaCl and 0.01M sodium phosphate whose pH has been adjusted to 7.4. The PDGF dialysate was then added at the rate of 5 milliliters per hour to a 25 cubic centimeter column containing an 8 milliliter bed volume of Blue Sepharose (Pharmacia) which has been previously equilibrated with several volumes of reagent fluid. The non-PDGF proteins pass through the Sepharose column unabsorbed while the PDGF fraction becomes bound to the gel particles. Afterwards, the gel bed is washed with 250 milliliters of reagent fluid. This is followed by elution of the purified PDGF with an eluting fluid comprising 50% (v/v) concentration of ethylene glycol in a 1M NaCl solution. Again, these volumetric specifications apply to a starting material of 500 platelet units. The biologically active fractions are pooled together as one volume and comprises a purified homogeneous PDGF fraction in a heterogeneous pool of polypeptides.

It is understood that means for concentrating the PDGF fractions other than Bio-Gel may be freely substituted so long as the biological activity of the fraction is substantially unimpaired. Moreover, agarose gels substituted with neutral alkyl groups other than Blue Sepharose and other fractional adsorption means may serve as the hydrophobic gel bed material. Similarly, other inorganic salt phosphate solutions may be employed as the reagent fluid and eluants other than 50% ethylene glycol are permissible substitutions so long as a biologically active PDGF fraction is eluted from the column. All of these alternative techniques and reagent substitutions are within the scope of the present invention.

D. Isolation of PDGF by Gel Electrophoresis Means

The preferred gel electrophoresis means for isolating the purified PDGF is the method described by Laemmli, Nature (London), 227:680-685 (1970) using sodium dodecyl sulphate polyacrylamide (12-15%) gels. The biologically active polypeptide eluants obtained from the Blue Sepharose absorption are dialyzed overnight at room temperature against several changes of a 0.02% aqueous solution of sodium dodecyl sulphate. The dialyzed PDGF material is then lyophilized and then reconstituted in a minimum volume (microliters) of a reagent solution comprising a mixture of 2.0% sodium dodecyl sulphate in 0.06M Tris.HCl which has been previously adjusted to pH 6.8 and then combined with 15% sucrose. The PDGF reagent solution is boiled for two minutes, without reduction, and applied to the gel along with synthetic molecular weight standards ranging in weight from 14,300-71,400 daltons. The gel is attached to the electrophoresis electrodes and subjected to electrophoresis (2mA/gel) for approximately 5-7 hours. All of the polypeptide fractions becomes separated and isolated within the gel according to their molecular weight as individual localized bands. The PDGF fractions are those localized bands of polypeptides migrating by weight which correspond to the 32,000 and 35,000 dalton range, as compared to the known synthetic molecular weight standards.

E. Localization and Direct Recovery of PDGF

Following electrophoresis, the gel is stained with dye reagent means comprising a dye solution and a destaining solution. The dye solution comprises an aqueous mixture of 10% acetic acid, 10% methanol and 0.5% of a dye such as Commassie Blue or Commassie Brilliant G-25 or R-250. As can be seen by referring to FIG. 1, these dye solutions combine with the localized polypeptides in the gel to make the polypeptides chromophoric. After the gel is destained, the colored polypeptides are visibly distinct and clearly distinguishable from the remainder of the translucent polyacrylamide gel. Although the dye reagent means combine with the PDGF and make them visually discernable, none of these dye reagents substantially impairs the biological activity of the PDGF.

Other dyes which are known to stain polypeptides within gels used in electrophoresis may be substituted as the dye reagent means so long as the biological activity of the PDGF fraction trapped in the polyacrylamide gel is not substantially impaired after becoming a chromophore. All such dye reagent substitutions are equivalent to those dyes specifically identified herein and are within the scope of the present invention.

To design the polyacrylamide gel, the gel columns are placed in a destaining solution consisting of an aqueous mixture of 10% acetic and 10% 2-propanol for several hours. The homogeneous PDGF polypeptides previously separated according to molecular weight by electrophoresis, are now visibly distinct as darkly colored bands in the translucent gel. In particular, as can be seen clearly in FIG. 1, the polypepetides having a molecular weight corresponding to 32,000 daltons and 35,000 daltons are clearly distinguishable. Following the staining, the gel column is rinsed with distilled water and the protein bands trapped in the gel corresponding to 32,000 daltons and 35,000 daltons respectively excised as a gel slice. The clear gel spaces between the desired protein bands are cut and the gel slice removed as a unit and placed in a borosilicate tube containing 0.5 milliliters of an eluant reagent fluid preferably comprising 2.0M ammonium bicarbonate and 0.04% sodium dodecyl sulphate.

The gel slice is minced and the chromophoric PDGF allowed to elute into the eluant reagent fluid for 8-12 hours at room temperature. The colored fluid is removed from each minced gel slice and placed in individual tubes. This elution procedure is repeated cyclically twice more, each cycle combining an additional 0.5 milliliters of the eluant reagent fluid with the minced gel slice to elute more PDGF. Some of the colored fluids containing PDGF may be combined with 1% human serum albumin for evaluation of specific biological activity. Should a more complete separation of Type I and Type II PDGF be desired, the eluant recovered as described above may be again subjected to the isolating, excising and eluting steps. By referring to FIGS. 2 and 3, Types I and II PDGF are shown after their second electrophoretic localization on 15% polyacrylamide gel. Each type is distinctly separated from the other, may be excised individually and eluted as a single pure active polypeptide.

As can be seen by reference to Table 1, each chromophoric PDGF obtained in the manner described herein retains full specific biological activity. The fraction corresponding to PDGF-I has a specific activity of 3,200 units and the PDGF-II has a specific activity of 2,600 units per microgram of protein. Moreover, each of the antecedent protein fractions obtained by completing a step of the method described herein also have substantial amounts of specific biological activity as shown in Table I. The effectiveness of each and every step of the process therefore can be verified by testing the antecedent protein fractions for their ability to specifically stimulate the synthesis of DNA and to initiate fibroblast cell division.

It will be appreciated that other methods to extract and purify PDGF may utilize only the localization and recovery steps of the present invention to advantage. It is expected in such situations, that a homogeneous or semipure polypeptide fraction comprising the PDGF will be present as but one fraction in a heterogeneous polypeptide pool. Nevertheless, the isolating of PDGF by gel electrophoresis means, the staining of PDGF within the gel with dye reagent means, the excising of the chromophoric band, and the eluting of the stained PDGF from the excised gel may be employed as previously described herein. These steps may be applied to recover any PDGF polypeptide fraction without regard to its source of origin or method of extraction and purification.

TABLE I

Purification of PDGF

| Purification Step | Protein, ug | PDGF Units | Recovery, % | Specific Activity Units/ug Protein |
|---|---|---|---|---|
| Platelet lysate | 78,000,000 | 2,600,000 | 100 | 0.0325 |
| Bio-Gel P-150 | 10,000 | 720,000 | 28 | 72 |
| Blue Sepharose | 900 | 460,000 | 18 | 510 |
| NaDodSO4/PAGE (12% polyacrylamide) | 60 | 172,000 | 6.5 | 2870 |
| PDGF-I (unreduced) | 30 | 96,000 | 3.7 | 3200 |
| PDGF-II (unreduced) | 20 | 52,000 | 2.0 | 2600 |

Estimates from fractionation of 500 clinically outdated human platelet units.

It is also apparent that the steps of isolating, staining, excising and eluting as described herein can be generally employed to localize and recover any homogeneous polypeptide from a heterogeneous pool of polypeptides. Only two conditions must be met: The polypeptide(s) of interest must be capable of migration within the gel electrophoresis means such that a complete separation of fractions by molecular weight will occur. The dye reagent selected must not substantially impair the characteristic activity associated with the polypeptide of interest. A polypeptide's characteristic activity is not substantially impaired if the activity of choice is not significantly modified or altered by combination with the selected dye reagent means.

The source, nature and use of the polypeptide of interest is inconsequential. Similarly, the particular activity chosen as characteristic of the polypeptide of interest is of no importance so long as the identifying characteristic is a true and reliable measure of the polypeptide. Localization and direct recovery of polypeptides ranging from 5,000 to 100,000 daltons may be achieved in this manner. Similarly, small protein fragments, polypeptide chains formed by reduction of multichain proteins, and enzymatically cleaned fractions all may be obtained using this process.

The present invention is not to be limited in scope nor restricted in form by the specific disclosure except by the claims appended hereto.

What is claimed is:

1. A process for extracting Platelet Derived Growth Factor from an aqueous suspension of platelets comprising the steps of:
   precipitating the polypeptide fraction comprising the Platelet Derived Growth Factor from the internal contents of the platelets;
   separating said polypeptide fraction comprising the Platelet Derived Growth Factor from said precipitant;
   purifying the Platelet Derived Growth Factor in said polypeptide fraction to homogenity;
   isolating said Platelet Derived Growth Factor using means for gel electrophoresis whereby said Platelet Derived Growth Factor is isolated as at least one localized band within said gel means after electrophoresis;

staining said localized band of Platelet Derived Growth Factor in said gel electrophoresis means with dye reagent means, whereby said isolated band becomes a biologically active chromophore visibly distinguishable from said gel electrophoresis means;

excising said chromophoric biologically active Platelet Derived Growth Factor from said gel electrophoresis means as a gel slice; and eluting said chromophoric Platelet Derived Growth Factor from said excised gel slice.

2. A process for extracting Platelet Derived Growth Factor from an aqueous suspension of platelets comprising the steps of:

fractionally precipitating the internal contents of said platelets with a plurality of reagents wherein the polypeptide fraction comprising the platelet derived growth factor is precipitated by organic precipitating reagent means;

separating said polypeptide fraction comprising the Platelet Derived Growth Factor from said precipitant using means for liquid chromatography;

purifying said Platelet Derived Growth Factor in said polypeptide fraction to homogenity using means for concentration of polypeptides and means for fractional adsorption of polypeptides;

isolating said Platelet Derived Growth Factor using means for gel electrophoresis, whereby said Platelet Derived Growth Factor is isolated as at least one localized band within said gel means after electrophoresis;

staining said localized band of Platelet Derived Growth Factor in said gel electrophoresis means with dye reagent means, whereby said isolated band becomes a biologically active chromophore visibly distinguishable from said gel electrophoresis means;

excising said chromophoric biologically active Platelet Derived Growth Factor from said gel electrophoresis means as a gel slice; and eluting said chromophoric Platelet Derived Growth Factor from said excised gel slice.

3. The process for extracting Platelet Derived Growth Factor as recited in claim 1 or 2 wherein said gel electrophoresis means includes polyacrylamide gel electrophoresis.

4. The process for extracting Platelet Derived Growth Factor as recited in claim 1 or 2 wherein said dye reagent means includes dyes selected from the group consisting of Commassie Blue, Commassie Brilliant Green, and R-250.

5. The process for extracting Platelet Derived Growth Factor as recited in claim 2 wherein said organic precipitating reagent means includes acetone.

6. The process for extracting Platelet Derived Growth Factor as recited in claim 2 wherein said liquid chromatography means includes ion exchange chromatography.

7. The process for extracting Platelet Derived Growth Factor as recited in claim 2 wherein said polypeptide fractional adsorption means includes reaction with Blue Sepharose.

8. The process for extracting Platelet Derived Growth Factor as recited in claim 2 wherein said polypeptide concentration means includes Bio-Gel filtration.

9. A process for extracting Platelet Derived Growth Factor from an aqueous suspension of platelets comprising the steps of:

fractionally precipitating the internal contents of platelets with a plurality of reagents whereby platelet derived growth factor is precipitated using acetone;

separating said platelet derived growth fraction from said precipitant using ion exchange chromatography means purifying said Platelet Derived Growth Factor to homogenity using Bio-Gel filtration means and Blue Sepharose adsorption means;

isolating said Platelet Derived Growth Factor using polyacrylamide gel electrophoresis means, whereby said Platelet Derived Growth Factor is isolated as at least one localized band within said gel means after electrophoresis;

staining said localized band of Platelet Derived Growth Factor within said gel means using dye reagent means whereby said localized band becomes a biologically active chromophore distinguishable from said gel means;

excising said chromophoric biologically active Platelet Derived Growth Factor from said gel means as a gel slice; and eluting said chromophoric Platelet Derived Growth Factor from said gel slice.

10. A process for the localization and direct recovering of homogeneous polypeptide fractions from a pool of heterogeneous polypeptides, said method comprising the steps of:

subjecting said heterogeneous peptide pool to means for gel electrophoresis whereby each of said homogeneous polypeptide fractions is isolated as a localized band within said gel means after electrophoresis;

staining said localized bands of homogeneous peptides localized in said gel electrophoresis means with dye reagent means whereby each of said localized bands becomes a biologically active chromophore visibly distinguishable from said gel means;

excising at least one of said chromophoric biologically active bands from said gel means as a gel slice; and eluting said chromophoric polypeptide from said gel slice.

11. The process for recovery of homogeneous polypeptides as recited in claim 10 wherein said gel electrophoresis means includes polyacrylamide gel electrophoresis.

12. The process for recovery of homogeneous polypeptides as recited in claim 10 wherein said dye reagent means includes a dye selected from the group consisting of Commassie Blue, Commassie Brilliant Green, and R-250.

* * * * *